United States Patent [19]
Altman et al.

[11] Patent Number: 5,976,874
[45] Date of Patent: Nov. 2, 1999

[54] PHENOTYPIC CONVERSION OF DRUG-RESISTANT BACTERIA TO DRUG-SENSITIVITY

[75] Inventors: Sidney Altman, Hamden; Cecilia Guerrier-Takada, New Haven, both of Conn.

[73] Assignee: Yale University, New Haven, Conn.

[21] Appl. No.: 08/911,886

[22] Filed: Aug. 15, 1997

Related U.S. Application Data

[60] Provisional application No. 60/023,675, Aug. 16, 1996, and provisional application No. 60/053,774, Jul. 25, 1997.

[51] Int. Cl.[6] ............................. C12N 15/52; C12N 15/74; A61K 31/70; C07H 21/00
[52] U.S. Cl. ............................ 435/320.1; 435/6; 435/32; 435/91.1; 435/91.2; 435/199; 514/44; 536/23.1; 536/23.2; 536/24.5; 424/93.2
[58] Field of Search .................................. 435/6, 32, 91.1, 435/91.2, 199, 320.1; 514/44; 536/23.1, 23.2, 24.5; 424/93.2

[56] References Cited

U.S. PATENT DOCUMENTS

| | | | |
|---|---|---|---|
| 5,168,053 | 12/1992 | Altman et al. | 435/6 |
| 5,180,818 | 1/1993 | Cech et al. | 536/23.1 |
| 5,624,824 | 4/1997 | Yuan et al. | 435/91.2 |
| 5,683,873 | 11/1997 | George et al. | 435/6 |
| 5,728,521 | 3/1998 | Yuan et al. | 435/6 |

FOREIGN PATENT DOCUMENTS

| | | |
|---|---|---|
| 321021 | 6/1989 | European Pat. Off. . |
| WO 88/04300 | 6/1988 | WIPO . |
| WO 89/05852 | 6/1989 | WIPO . |
| WO 91/04319 | 4/1991 | WIPO . |
| WO 91/04324 | 4/1991 | WIPO . |
| WO 92/03566 | 3/1992 | WIPO . |
| WO 95/24489 | 9/1995 | WIPO . |
| WO 95/27480 | 10/1995 | WIPO . |
| WO 95/32283 | 11/1995 | WIPO . |
| WO 96/18733 | 6/1996 | WIPO . |
| WO 96/21731 | 7/1996 | WIPO . |

OTHER PUBLICATIONS

Altman, (1993), "RNA Enzyme–Directed Gene Therapy," *Proc. Natl. Acad. Sci. USA* 90, 10898–10900.

Altman et al., "Recent Studies of Ribonuclease P," *FASEB J.* 7:7–15 (1993).

Cech, "Self splicing of Group I introns," *Annu. Rev. Biochem.* 59:543–568 (1990).

Clerget et al., "The Structure of R1drd19: A Revised Physical Map of the Plasmid," *Mol. Gen. Genet.* 181:183–191 (1981).

Felgner, et al. (1989), "Cationic Liposome–Mediated Transfection," *Nature*, 337, 387–388.

Felgner, et al., (1987), "Lipofection: A Highly Efficient, Lipid–Mediated DNA–Transfection Procedure," *Proc. Natl. Acad. Sci USA,* 84, 7413–7417.

(List continued on next page.)

*Primary Examiner*—Ponnathapu Achutamurthy
*Assistant Examiner*—William W. Moore
*Attorney, Agent, or Firm*—Arnall Golden & Gregory, LLP

[57] ABSTRACT

External guide sequences ("EGS") can be used to promote RNAase P-mediated cleavage of RNA transcribed from plasmids and other genetic elements which confer drug resistance on bacterial cells. Such cleavage can render the bacteria drug sensitive. In a preferred embodiment, a vector encoding an EGS is administered to an animal or human harboring antibiotic resistant bacterial cells such that the EGS is expressed in the bacterial cells, the EGS promotes RNAase P-mediated cleavage of RNA involved in conferring antibiotic resistance to the cells, and the cells are rendered antibiotic sensitive. A preferred form of administration is via inoculation of the animal or human with cells containing genes for appropriate EGSs on promiscuous plasmids. These plasmids will spread quickly through the antibiotic-resistant population of bacterial cells, thereby making the cells susceptible to antibiotic therapy.

14 Claims, 5 Drawing Sheets

OTHER PUBLICATIONS

Felgner (1990), "Particulate Systems and Polymers for In Vitro and In Vivo Delivery of Polynucleotides," *Advanced Drug Delivery Reviews*, 5:163–187 (1990).

Forster and Altman, "External Guide Sequences for an RNA Enzyme," *Science* 238:407–409 (1990).

Guerrier–Takada et al., "Artificial Regulation of Gene Expression in *Escherichia coli* by RNase P," *Proc. Natl. Acad. Sci. USA* 92:11115–11119 (1995).

Kim, et al., (1983), "Preparation of Multivesicular Liposomes," *Biochim. Biophys. Acta*, 728, 339–348.

Kufel and Kirsebom, "Different Cleavage Sites are Aligned Differently in the Active Site of M1 RNA, the Catalytic Subunit of *Escherichia coli* RNase P," *Proc. Natl. Acad. Sci. USA* 93:6085–6090 (1996).

Lee, et al., (1992), "Recognition of Liposomes by Cells: In Vitro Binding and Endocytosis Mediated by Specific Lipid Headgroups and Surface Charge Density," *Biochim. Biophys. Acta.,* 1103, 185–197.

Li and Altman, "Cleavage by RNase P of gene N mRNA Reduces Bacteriophage λ Burst Size," *Nucleic Acids Res.* 24:835–842 (1996).

Liu and Altman, "Inhibition of Viral Gene Expression by the Catalytic RNA Subunit of RNase P from *Escherichia coli,*" *Genes Dev.* 9:471–480 (1995).

Liu, et al. (1992), "Role of Liposome Sizes and RES Blockade in Controlling Biodistribution and Tumor Uptake of $GM_1$–Containing Liposomes*," *Biochim. Biophys. Acta,* 1104:95–101 (1992).

Meyer and Schottel, "Characterization of cat messenger RNA Decay Suggests that Turnover Occurs by Endonucleolytic Cleavage in a 3' to 5' Direction," *Mol. Microbiol.* 6:1095–1104 (1992).

Meynell and Datta, "Mutant Drug Resistant Factors of High Transmissibility," *Nature* 214:885–887 (1967).

Rosenberg et al., "Vectors for Selective Expression of Cloned DNAs by T7 RNA Polymerase," *Gene* 56:125–135 (1987).

Rossi, et al., (1991), "Exploring the Use of Antisense, Enzymatic RNA Molecules (Ribozymes) as Therapeutic Agents," *Antisense Res. Dev.,* 1, 285–288.

Sedgwick and Morga, "Locating, DNA Sequencing, and Disrupting Yeast Genes Using Tagged TN1000," *Meth. in Molec. Gen.* 3:131–140 (1994).

Studier and Moffat, "Use of Bacteriophage T7 RNA Polymerase to Direct Selective High–Level Expression of Cloned Genes," *J. Mol. Biol.* 189:113–130 (1986).

Symons, (1992) "Small Catalytic RNAs," *Annu. Rev. Biochem.* 61, 641–671. Takle et al., *Antisense and Nucleic Acid Drug Dev.* 7:177–185 (1997).

Wang et al., "Highly Efficient DNA Delivery Mediated by pH–Sensitive Immunoliposomes," *Biochem.,* 28:9508–9514 (1989).

Wertman et al., "Host/Vector Interactions Which Affect the Viability of Recombinant Phage Lambda Clones," *Gene* 49:253–262 (1986).

Yuan, et al., (1992), "Targeted Cleavage of mRNA by Human RNase P," *Proc. Natl. Acad. Sci. USA* 89, 8006–8010.

Zucker and Stiegler, "Optional Computer Folding of Large RNA Sequences Using Thermodynamics and Auxiliary Information," *Nucl. Acids Res.* 9:133–148 (1981).

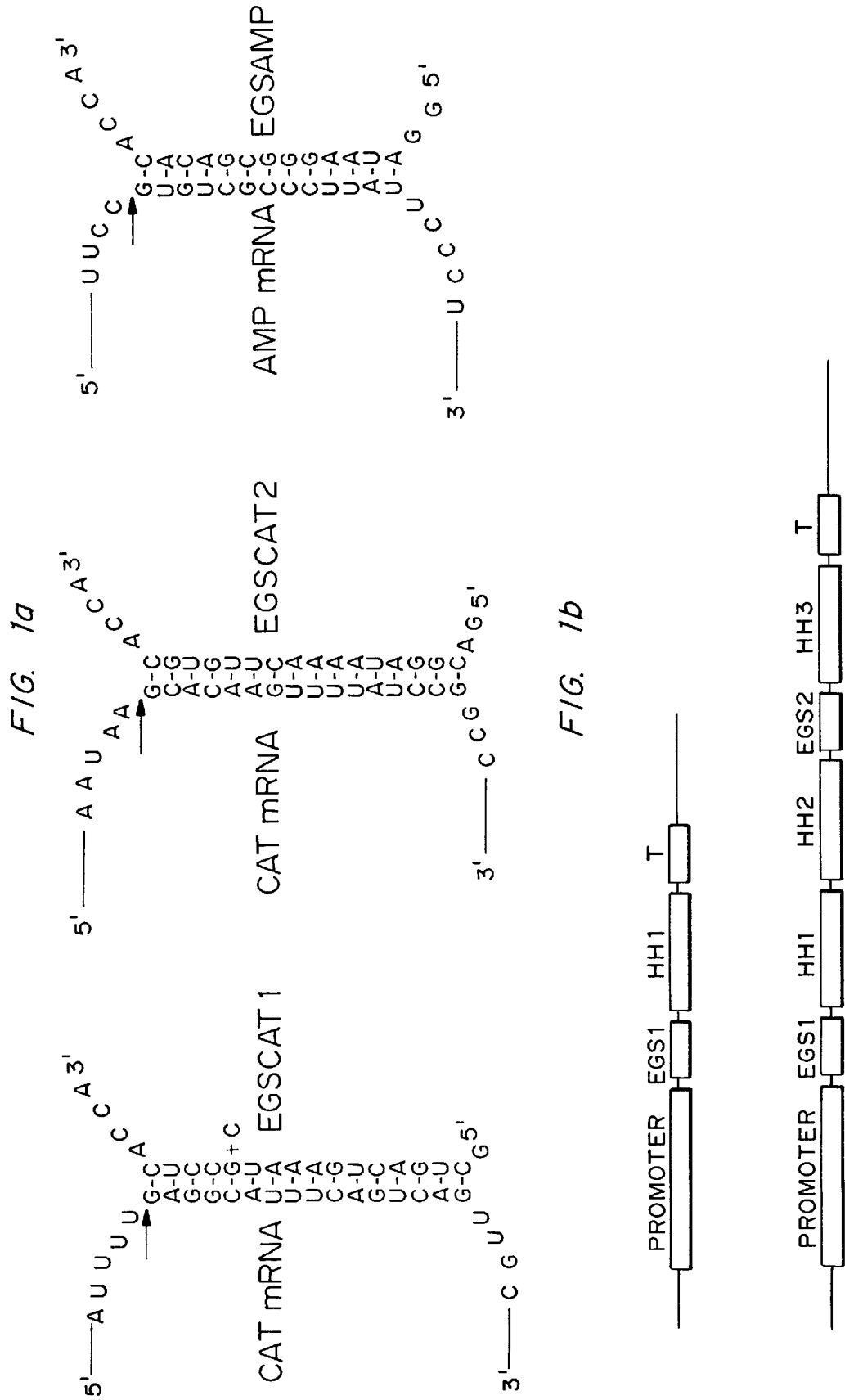

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 75 bases
      (B) TYPE: nucleic acid
      (C) STRANDEDNESS: single
      (D) TOPOLOGY: linear (ii) MOLECULE TYPE: RNA (iii) HYPOTHETICAL: NO (iv) ANTI-SENSE: no (xi) SEQUENCE DESCRIPTION: SEQ ID NO:1:

```
GCUGACUGAA AUGCCUCACC AGGUCACCGG AUGUGCUUUC CGGUCUGAUG AGUCCGUGAG      60

GACGAAACCU GGAUC                                                       75
```

(2) INFORMATION FOR SEQ ID NO:2:

(i) SEQUENCE CHARACTERISTICS:
      (A) LENGTH: 73 bases
      (B) TYPE: nucleic acid
      (C) STRANDEDNESS: single
      (D) TOPOLOGY: linear (ii) MOLECULE TYPE: RNA (iii) HYPOTHETICAL: NO (iv) ANTI-SENSE: no (xi) SEQUENCE DESCRIPTION: SEQ ID NO:2:

GGAUAAGGGC GACACACCAG GUCACCGGAU GUGCUUUCCG GUCUGAUGAG UCCGUGAGGA    60

CGAAACCUGG AUC                                                      73

(2) INFORMATION FOR SEQ ID NO:3:

(i) SEQUENCE CHARACTERISTICS:
            (A) LENGTH: 20 bases
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: no (xi) SEQUENCE DESCRIPTION: SEQ ID NO:3:

UUGAGGCAUU UCAGUCAGUU                                                20

(2) INFORMATION FOR SEQ ID NO:4:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: no (xi) SEQUENCE DESCRIPTION: SEQ ID NO:4:

UUCCGUGUCG CCCUUAUUCC CU                                             22

(2) INFORMATION FOR SEQ ID NO:5:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: no (xi) SEQUENCE DESCRIPTION: SEQ ID NO:5:

GACGGAUAAA ACUUGUGCAC CA                                             22

(2) INFORMATION FOR SEQ ID NO:6:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: RNA -continued (iii) HYPOTHETICAL: NO (iv) ANTI-SENSE: no (xi) SEQUENCE DESCRIPTION: SEQ ID NO:6:

AAUAAGCACA AGUUUUAUCC GGCC                               24

PHENOTYPIC CONVERSION OF DRUG-RESISTANT BACTERIA TO DRUG-SENSITIVITY

CROSS-REFERENCE TO RELATED APPLICATIONS

This application claims benefit of U.S. Provisional Application No. 60/023,675, filed Aug. 16, 1996, and the U.S. Provisional Application 60/053,774, by Sidney Altman and Cecilia Guerrier-Takada entitled "Conversion of Drug-resistant Bacteria to Drug-sensitive Bacteria", filed Jul, 25, 1997.

BACKGROUND OF THE INVENTION

The present invention is generally in the field of external guide sequences, and specifically in the use of external guide sequences to convert the phenotype of drug-resistant pathogens to a drug-sensitive phenotype.

Drug resistance in pathogenic bacteria is a problem of major clinical importance. When public hygiene practices are careless, plasmids carrying genes for drug resistance spread rapidly through both animal and human populations through various routes. Nosocomial infections (that is, hospital acquired) are most problematic in terms of drug resistance, with many multi-drug-resistant strains of *Staphylococcus aureus, S. epidermatities, enterococci,* and *Escherichia coli* present in hospitals leading to life-threatening illness, especially in immunocompromised patients. The standard approach to this problem has consisted of attempts to discover new drugs to which the bacteria are sensitive, an expensive and time-consuming process. To further complicate matters, bacteria continue to mutate to acquire resistance to newly developed drugs.

It is therefore an object of the present invention to provide a method for converting the phenotype of drug-resistant bacteria to a drug-sensitive phenotype.

It is another object of the present invention to provide a composition for converting the phenotype of drug-resistant bacteria to a drug-sensitive phenotype.

BRIEF SUMMARY OF THE INVENTION

External guide sequences ("EGS") can be used to promote RNAase P-mediated cleavage of RNA transcribed from plasmids and other genetic elements which confer drug resistance on bacterial cells. Such cleavage can render the bacteria drug sensitive. In a preferred embodiment, a vector encoding an EGS is administered to an animal or human harboring antibiotic resistant bacterial cells such that the EGS is expressed in the bacterial cells, the EGS promotes RNAase P-mediated cleavage of RNA involved in conferring antibiotic resistance to the cells, and the cells are rendered antibiotic sensitive. A preferred form of administration is via inoculation of the animal or human with cells containing genes for appropriate EGSs on promiscuous plasmids. These plasmids will spread quickly through the antibiotic-resistant population of bacterial cells, thereby making the cells susceptible to antibiotic therapy.

As demonstrated by the example, synthetic genes coding for EGSs have been inserted into plasmids compatible with other plasmids bearing drug resistance genes in *Escherichia coli*. The EGSs, designed to form complexes with mRNA encoded by genes for either ampicillin or chloramphenicol resistance, direct RNAase P to cleave the targeted mRNAs, thereby converting the phenotype of drug-resistant cells to drug-sensitivity.

BRIEF DESCRIPTION OF THE DRAWINGS

FIG. 1A is a schematic of EGSs EGSCAT1 (nucleotides 1 to 21 of SEQ ID NO:1), EGSCAT2 (SEQ ID NO:5), and EGSAMP (nucleotides 1 to 19 of SEQ ID NO:2), targeted to Cat mRNA (EGSCAT1 and EGSCAT2) and Amp mRNA (EGSAMP) substrates, the relevant portions of which are shown (SEQ ID NO:3, SEQ ID NO:6, and SEQ ID NO:4, respectively).

FIG. 1B is a schematic representation of synthetic genes for either one EGS alone or two EGSs in tandem. HH1, HH2, and HH3 are hammerhead sequences. T is a terminator sequence. The promoter and terminator sequences are derived either from phage T7 or *E. coli*.

DETAILED DESCRIPTION OF THE INVENTION

Figure 2A:
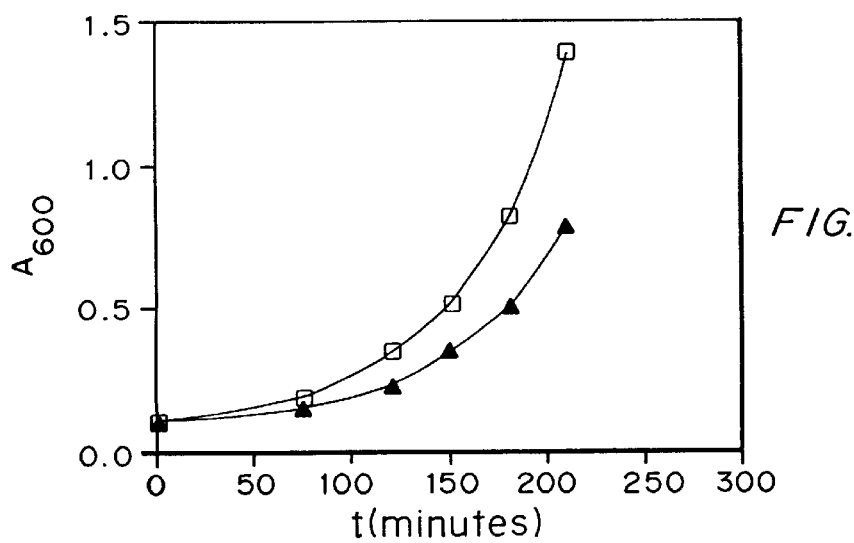
FIGS. 2A, 2B, and 2C are is growth curves of BL21(DE3) cells carrying two plasmids: pACYC184+pKBEGSAMP (open squares) and pACYC184+pKBEGSCAT1 (triangles), graphing growth over time (min) at 50 Carb/5 Cm (FIG. 2A), 50 Carb/70 Cm (FIG. 2B), and 500 Carb/5 Cm (FIG. 2C).

A method of converting the phenotype of drug-resistant bacteria to a drug-sensitive phenotype has been developed. This method preferably makes use of external guide sequences to direct cleavage by RNAase P of RNA molecules involved in conferring drug-resistance on bacteria. Such cleavage can render the bacteria drug sensitive. This method should be useful both for veterinary purposes and as a human clinical therapy. This method can also be used to convert the phenotype of drug-resistant bacteria in other settings. While the present method is directed to the targeting of drug-resistant bacteria, a similar method can be employed to convert the phenotype of other pathogens or, indeed, plant or animal cells. This method can take advantage of the ability of vectors such as promiscuous plasmids to spread quickly through affected populations.

In a preferred embodiment of the disclosed method, external guide sequences are designed to form hydrogen-bonded complexes with the mRNAs encoded by drug resistance genes, for example, those coding for chloramphenicol acetyltransference ($Cm^R$) or β-lactamase ($Amp^R$). When the complexes are formed, they are recognized as substrates by the endogenous endonuclease RNAase P (Altman et al., *FASEB J.* 7:7–15 (1993)) and the targeted mRNA is cleaved and inactivated, thereby rendering the host cells drug sensitive. This technology has been used successfully to decrease levels of gene expression in both bacteria (Altman et al. (1993)) and mammalian cells in tissue culture (Yuan et al., *Proc. Nat. Acad. Sci. USA* 89:8006–8010 (1992); Liu and Altman, *Genes Dev.* 9:471–480 (1995)). External guide sequences can be used directly, or the same mechanism that is used in nature to spread drug resistance among human and animal populations can be employed to transmit appropriate EGS-encoding genes to drug-resistant bacteria. That is, the genes coding for EGSs can be inserted into promiscuous plasmids (Meynell and Datta, *Nature* 214:885–887 (1967); Clerget et al., *Mol. Gen. Genet.* 181:183 (1981); Thomas, ed., "Promiscuous plasmids of Gram-negative Bacteria" (Academic Press (London), 1989); Hardy, ed., "Plasmids: a practical approach", 2nd ed. (Oxford University Press (Oxford), 1993)) and these plasmids can be introduced into drug-resistant bacterial cultures.

External Guide Sequences and Ribozymes

Ribonucleic acid (RNA) molecules can serve not only as carriers of genetic information, for example, genomic retroviral RNA and messenger RNA (mRNA) molecules, and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The use of catalytic RNA in commercial applications, particularly in therapeutics, is reviewed by Altman, *Proc. Natl. Acad. Sci. USA* 90:10898–10900 (1993); Symons, *Annu. Rev. Biochem.* 61:641–671 (1992); Rossi et al., *Antisense Res. Dev.* 1:285–288 (1991); and Cech, *Annu. Rev. Biochem.* 59:543–568 (1990). Several classes of catalytic RNAs have been described, including intron-derived ribozymes (WO 88/04300; see also, Cech, *Annu. Rev. Biochem.* 59:543–568 (1990)), hammerhead ribozymes (WO 89/05852 and EP 321021 by GeneShears), axehead ribozymes (WO 91/04319 and WO 91/04324 by Innovir), as well as RNAase P.

RNAase P is a ribonucleoprotein having two components, an RNA component and a protein component. RNAase P is responsible for the cleavage which forms the mature 5' ends of all transfer RNAs. The RNA component of RNAase P is catalytic. RNAase P is endogenous to all living cells examined to date. During the studies on recognition of substrate by RNAase P, it was found that *E. coli* RNAase P can cleave synthetic tRNA-related substrates that lack certain domains, specifically, the D, T and anticodon stems and loops, of the normal precursor tRNA structure. A half-turn of an RNA helix, at least one nucleotide upstream of the half-turn, and a 3' proximal CCA sequence contain sufficient recognition elements to allow the reaction to proceed. The 5' proximal sequence of the RNA helix does not have to be covalently linked to 3' proximal sequence of the helix. The 3' proximal sequence of the stem can be regarded as a "guide sequence" because it identifies the site of cleavage in the 5' proximal region through a base-paired region. Oligonucleotides can be designed to direct RNAase P to cleave any desired RNA molecule. Such oligonucleotides are referred to as external guide sequences and their design and use are described in U.S. Pat. No. 5,168,053 to Altman et al.

Any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide). This is described in WO 92/03566 and Forster and Altman, *Science* 238:407–409 (1990). EGS/RNAase P-directed cleavage of RNA has been developed for use in eukaryotic systems as described by Yuan et al., *Proc. Natl. Acad. Sci. USA* 89:8006–8010 (1992). As used herein, "external guide sequence" and "EGS" refer to any oligonucleotide that forms an active cleavage site for RNAase P in combination with a target RNA.

The disclosed method makes use of RNAase P endogenous to the bacteria in which the RNA to be cleaved is located. When a vector encoding an EGS enters the bacteria and the EGS is expressed, the EGS can form a complex with the target RNA. Such a EGS/target RNA complex is then recognized as a substrate and the target RNA is cleaved by the endogenous RNAase P.

External Guide Sequences. An external guide sequence for promoting cleavage by prokaryotic RNAase P is referred to herein as prokaryotic EGS. The critical elements of a prokaryotic EGS are (1) nucleotide sequence which specifically binds to the targeted RNA substrate to produce a short sequence of base pairs 3' to the cleavage site on the substrate RNA, referred to as the complementary nucleotides, and (2) a terminal 3'-NCCA, where N is any nucleotide, preferably a purine. The complementary nucleotides can include any number of nucleotides that allows hybridization to nucleotides 3' to the site to be cleaved. It is preferred that the complementary nucleotides include at least fifteen nucleotides. It is also preferred that the complementary nucleotides include a number of nucleotides sufficient to hybridize uniquely to the nucleotides 3' to the site to be cleaved. It is most preferred that the complementary nucleotides have about fifteen nucleotides. It is not critical that all nucleotides be complementary, although the efficiency of the reaction will decrease as the degree of complementarity decreases. The rate of cleavage is dependent on the RNAase P and the solution structure of the hybrid substrate, which includes the targeted RNA and the presence of the 3'-NCCA in the hybrid substrate.

Vectors

Any vectors that can be transferred into bacterial cells can be used in the disclosed method to deliver genes encoding EGSs to bacterial cells. It is preferred that the vector be capable of transfer from one bacterial cell to others. Vectors for use in the disclosed method can be derived from the same vectors that typically encode genes specifying drug resistance which are the targets of the disclosed method. Such vectors include transmissible plasmids, episomal vectors, and viral vectors that integrate into the host chromosome with a high frequency. Most preferred are promiscuous plasmids. A promiscuous plasmid is one that is mutated to ensure rapid and efficient, constitutive, transfer to compatible bacteria. Preferred promiscuous plasmids include R1-drd-19 (Meynell and Datta (1967); Clerget et al. (1981)) and R388 (Sedgwick and Morga, *Meth. in Molec. Gen.* 3:131–140 (1994)). It is preferred that the vector be a vector that can be transferred to, and function in, the target bacteria. For this purpose, many suitable vectors, including promiscuous plasmids, are known for a wide variety of bacterial species.

Target Bacteria for Phenotypic Conversion

The method described herein for phenotypic conversion of drug resistance can be applied to any species of bacteria that produces an RNA involved in conferring drug resistance on the bacteria. The disclosed method can be used to convert the phenotype of drug-resistant bacteria to a drug-sensitive phenotype in any setting. Preferred target bacteria are those that infect, colonize, or otherwise grow in or on plants or animals, including humans. Preferred target bacteria can harbor transmissible plasmids, episomal vectors, or viral vectors that integrate into the host chromosome with a high frequency which carry drug resistance markers.

Preferred target bacterial cells are those that colonize, infect, or otherwise grow in or on animals. Particularly preferred are bacterial cells that colonize, infect, or grow in or on skin, in the gastrointestinal tract or in the respiratory tract. Also preferred are bacterial cells that colonize, infect, or grow in the urogenital tract. Some preferred bacterial cells belong to one of the families Enterobacteriaceae, Micrococcaceae, Vibrionaceae, Pasteurellaceae, Mycoplasmataceae, or Rickettsiaceae. Within these families, preferred bacterial cells belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, or Ehrlichia. Particular preferred bacterial cells are those that belong to the family Enterobacteriaceae.

Preferred bacterial cells belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Camylobacter, Arcobacter, Wolinella, Heliobacter, Achomobacter, Acinetobacter, Agrobacterium, Alcaligenes, Chryseomonas, Comamonas, Eikenella, Flavimonas, Flavobacterium, Moraxella, Oligella, Pseudomonas, Skewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira, or Chlamydiae.

Particularly preferred are bacterial cells that belong to one of the genera Salmonella, Shigella, Escherichia, Enterobacter, Serratia, Proteus, Yersinia, Citrobacter, Edwardsiella, Providencia, Klebsiella, Hafnia, Ewingella, Kluyvera, or Morganella. Most preferred are bacterial cells that belong to one of the genera Salmonella or Escherichia.

Mutation of the original drug-resistant bacteria to a novel form of resistance that prevents the EGS from exerting its effect on bacterial phenotype is unlikely since a single base mismatch in the complex with the target mRNA will not significantly alter recognition by RNAase P (Kufel and Kirsebom, *Proc. Nat. Acad. Sci. USA* 93:6085–6090 (1996)). Additionally, promiscuous plasmids are available for use with a variety of clinically important Gram-positive as well as Gram-negative bacteria so the disclosed method can be used against a wide variety of bacteria.

Compositions For Phenotypic Conversion of Bacterial Cells

EGS molecules can be used directly to convert the phenotype of a bacterial cell. Alternatively, an EGS can be delivered to a bacterial cell via a vector containing a sequence which encodes and expresses the EGS molecule specific for a particular RNA. In either case, it is preferred that the EGS is used in combination with a pharmaceutically acceptable carrier to form a pharmaceutical composition when the targeted bacterial cell is in an animal or patient.

A variety of carriers are available for administering EGS molecules, or DNA encoding EGS molecules, to animals and patients. For example, in general, the EGS molecules, or DNA sequences encoding the EGS molecules, can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., *Biochim. Biophys. Acta*, 728:339–348 (1983); Liu et al., *Biochim. Biophys. Acta*, 1104:95–101 (1992); and Lee et al., *Biochim. Biophys. Acta*, 1103:185–197 (1992); Wang et al., *Biochem.*, 28:9508–9514 (1989)). Nucleic acids to be delivered can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the nucleic acid molecules to be encapsulated, and the resulting hydrated lipid vesicles or liposomes encapsulating the material can then be washed by centrifugation and can be filtered and stored at 4° C. Alternatively, nucleic acid molecules can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium ("DOTMA," see Felgner et al., *Proc. Natl. Acad. Sci USA*, 84:7413–7417 (1987); Felgner et al., *Nature*, 337:387–388 (1989); Felgner, *Advanced Drug Delivery Reviews*, 5:163–187 (1990)).

A preferred form of microparticle for delivery of nucleic acid molecules are heme-bearing microparticles. In these microparticles, heme is intercalated into or covalently conjugated to the outer surface of the microparticles. Preferred lipids for forming heme-bearing microparticles are 1,2-dioleoyloxy-3- (trimethylammonium) propane (DOTAP) and dioleoyl phosphatidyl ethanolamine (DOPE). The production and use of heme-bearing microparticles are described in PCT application WO 95/27480 by Innovir. Nucleic acid can also be encapsulated by or coated on cationic liposomes which can be injected intravenously into a mammal.

For delivery to bacterial cells infecting an animal, liposomes containing EGS molecules, or DNA encoding these molecules, can be administered systemically, for example, by intravenous or intraperitoneal administration. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect. Delivery of nucleic acids using porphyrins is described below.

Compositions including various polymers such as the polylactic acid and polyglycolic acid copolymers, polyethylene, and polyorthoesters and the EGS molecules, or DNA encoding such molecules, can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, Johnson and Lloyd-Jones, eds., *Drug Delivery Systems* (Chichester, England: Ellis Horwood Ltd., 1987), which can effect a sustained release of the therapeutic nucleic acid compositions to the immediate area of the implant.

Nucleic acids, such as external guide sequences, and vectors encoding external guide sequences, can also be delivered to cells using macrocyclic compounds as described in PCT application WO95/27480. In preferred embodiments, the macrocyclic compounds are porphyrins or phthalocyanins; in the most preferred embodiment, the porphyrins are water soluble. The nucleic acid to be delivered has a net overall negative charge; the macrocyclic compound has a net overall positive charge under physiological conditions. As a result, the nucleic acid to be delivered is ionically bound to the macrocyclic compound until it and the bound nucleic acids are internalized in the targeted cells.

Vector Transfer

One embodiment of the disclosed method operates by delivery of vectors encoding EGSs targeted to RNA involved in conferring drug resistance on target bacteria to the target bacteria. EGS molecules can be delivered via a vector containing a sequence which encodes and expresses the EGS molecule specific for a particular RNA. A preferred composition comprises a cell containing a vector encoding an EGS. Such cells can be used to transfer the vector into target bacterial cells.

For use as a clinical therapeutic tool for any animals (for example, chickens, cows, horses, dogs, cats, and humans) that harbor bacteria that are hosts for transmissible drug resistance vectors of the kind described here, a series of EGSs can be prepared in advance that are directed against a set of mRNAs encoded by various drug resistance genes and cloned into appropriate vectors. Multiple EGSs can be transcribed together on the same transcript. In such cases it is preferred that cis-cleaving ribozymes be included in the transcripts to cleave the transcript into individual EGSs (see Examples 1 and 2).

Vector-mediated delivery involves the infection of the target bacterial cells with a self-replicating or a non-replicating system, such as a modified viral vector or a plasmid, which produces a large amount of the EGS encoded by the vector. Vector-mediated delivery produces a sustained amount of EGS molecules. It is substantially cheaper and requires less frequent administration than a direct delivery such as intravenous injection of the EGS molecules.

Vector transfer is preferably accomplished by adapting vectors which are naturally transferred between bacterial cells. This both provides a ready means of transfer at the site of bacterial infection and allows delivery of the vectors (and the encoded EGSs) by administration of, or inoculation with, bacterial cells harboring the vectors. Such a means of delivery can enhance the effectiveness of the vector by protecting the vector from nuclease degradation and delivering the vector to the site of infection. Sites of severe infections by drug-resistant bacteria (for example, intestine, skin, eye, ear, mammary gland) can then be inoculated with cultures of bacteria harboring the set of "therapeutic" vectors encoding the EGSs and, after a suitable interval to allow for the plasmids that encode the EGSs to be transmitted to the entire population, the appropriate antibiotic can be administered to the patient in which the infecting bacteria has now been rendered drug sensitive.

Transferring Bacteria

As described above, vectors encoding EGSs targeting RNA involved in conferring drug resistance on bacteria are preferably administered in, and transferred to the resistant bacteria, via host bacterial cells. Such host bacteria from which a vector is transferred to resistant bacteria is referred to herein as transferring bacteria. Any bacteria which can harbor one of the disclosed vectors and which will allow or mediate its transfer to a target bacterial cell can be used in the disclosed method. Preferred transfer bacteria are of the same genus or species of the target bacteria. Also preferred are bacteria which can colonize the same environments (such as gastrointestinal tract, respiratory tract, and the surface of plants) as the target bacteria and which are known to transfer genetic elements to the target bacteria. For use in animals or humans, preferred transfer bacteria include enteric bacteria and other bacteria that can colonize or grow in the gastrointestinal tract, and other bacteria that can colonize or grow in the respiratory tract. Especially preferred as transfer are strains of *E. coli*.

Phenotypic Conversion Using Promiscuous Plasmids

The following example provides an illustration of phenotypic conversion of drug-resistant bacteria using promiscuous plasmids. Synthetic EGS genes can be cloned into a plasmid such as R1-drd-19 (or R388) (Meynell and Datta (1967); Clerget et al. (1981)), a "promiscuous" plasmid. This is preferably accomplished by cloning the EGS gene into a transposon (for example, TN1000 or a suitable derivative such as TNΔEcoRI) and then transferring it to the promiscuous plasmid (Sedgwick and Morga (1994)) such as R388, to make a "tagged" transposon. R388 can be used directly or it can be used to transfer the transposon to R1-drd-19. To accomplish the latter, cells harboring R1-drd-19 can be transformed with R388, suitably compatible, and selected with appropriate drug markers for stable integration of the tagged transposon into R1-drd-19. The selection is arranged to disrupt, if necessary, a gene for drug resistance that may be the same as the target gene in the pathogenic population. For example, a gene for $Amp^R$ in R1-drd-19 would be replaced with an EGS targeted to $Amp^R$ mRNA.

To analyze the rate of phenotypic conversion with the disclosed method, an exponentially growing culture of *E. coli* (approximately $10^8$/ml) that is resistant to either Cm or Amp is first inoculated with about approximately $10^2$ cells/ml. Aliquots of this culture are taken at various intervals and tested for drug sensitivity. The kinetics of conversion of the culture to total drug sensitivity are plotted. The interval for phenotypic conversion should be correlated with the size of the inoculum. Conversion should not be due to the bacteria that contain EGS genes in the second inoculum overgrowing the culture. The bacteria in the final sample should still have the same chromosomal genotype as the initial, drug-resistant culture.

The disclosed method of phenotypic conversion can be optimized by, for example, searching for more sites in the target mRNA that will hybridize efficiently with an EGS to form very susceptible substrates for RNase P, by cloning multiple EGS genes (that will hybridize with the same and/or different sites in the target mRNA) into the carrier plasmid, by increasing the copy number of the plasmid and by increasing promoter strength upstream from the EGS genes thereby elevating the EGS:target mRNA ratio. Several aspects of these strategies are tested in Example 2.

Although described primarily with reference to delivery of EGS in vivo, it will be recognized by those skilled in the art that the same delivery system can be used for laboratory reagents for cell cultures and in diagnostic assays.

The present invention will be further understood by reference to the following non-limiting example. Abbreviations include EGS—external guide sequence; ptRNA—precursor tRNA; Cm—chloramphenicol; Amp—ampicillin.

EXAMPLES

Example 1

Phenotypic Conversion of Drug-resistant Bacteria

EGSs directed against the $Cm^R$ (cat) or $Amp^R$ (bla) mRNAs were designed and tested in vitro. The EGSs were designed to hydrogen-bond to sixteen or thirteen nucleotides, respectively, in the target mRNAs to make structures that resemble the aminoacyl stem of a tRNA and that terminate in the sequence ACCA that is common to all tRNAs. These sequences were initially cloned into pUC19 (a high copy number plasmid that harbors the gene for $Amp^R$) that is compatible with pACYC184 (a low copy number plasmid that harbors the $Cm^R$ gene) behind either a bacteriophage T7 promoter or an E. coli promoter (for the gene for M1 RNA) and followed by a cis-cleaving hammerhead ribozyme (see FIG. 1B, top).

The host bacterial strain for these examples was E. coli B strain BL21(DE3), F-ompT[lon]hsdS$_B$ (r$_B$-m$_B$-) with DE3, a λ prophage carrying the T7 RNA polymerase gene (Studier and Moffat, J. Mol. Biol. 189:113–130 (1986)). EGSs were constructed as follows: EGSs directed against $Cm^R$, GCUGACUGAAAUGCCUCACCA (EGSCAT1; nucleotides 1 to 21 of SEQ ID NO: 1) and GACGGAUAAAACUUGUGCACCA (EGSCAT2; SEQ ID NO:5), or $Amp^R$, GGAUAAGGGCGACACACCA (EGSAMP; nucleotides 1 to 19 of SEQ ID NO:2), were designed to hydrogen-bond to 16 bp (positions 67–82 and 156–171 in the coding region of the cat gene) and 13 bp sequences (positions 20–32 in the coding region of the bla gene), respectively, in the appropriate target mRNA to make a structure that resembles the aminoacyl stem of a tRNA and that terminates in the sequence CCA, which is common to all tRNAs. These EGSs are shown in FIG. 1A. For all EGSs constructed under T7 RNA polymerase control, inserts were cloned into pUC19 that was lacking a Pvu II—Pvu II fragment of 322 bp. DNA oligonucleotides containing the sequences for the T7 promoter, the various EGSs used and a hammerhead core of 57 nucleotides having the sequence CCAGGUCACCGGAUGUGCUUUCCGGUCUGAUGA GUCCGUGAGGAC GAAACCUGGAUC (nucleotides 19 to 75 of SEQ ID NO:1; the underlined sequence is the 3' terminus of the EGS) were ligated to a Bam HI-Hind III fragment containing the T7 terminator sequence (Guerrier-Takada et al., Proc. Natl. Acad. Sci. USA 92:11115–11119 (1995)). This DNA fragment was obtained from pET3040 (Rosenberg et al., Gene 56:125–135 (1987)). After cloning into the pUC vector, DNAs from transformants obtained were sequenced to verify that the proper sequence was present. The plasmids obtained were pT7EGSCAT1 and pT7EGSAMP. Plasmid pNT7APHH encodes an EGS directed against mRNA for alkaline phosphatase.

Plasmids with EGSs under the control of the E. coli promoter for M1 RNA were constructed as follows: The same inserts as noted above were cloned between the Bam HI and Hind III sites of pKB283, which is a pUC19 derivative with a 283 bp Kpn I-Bam HI insert that contains the promoter region for the gene encoding M1 RNA (rnpB). Plasmid pACYC184 was obtained from New England Biolabs.

E. coli resistant to Cm and not harboring pUC19 or its derivatives were transformed with the plasmids that contained these synthetic genes. Cultures were grown from single colony isolates and their growth properties were tested in the presence of various concentrations of Cm or Amp. Studies of the growth of cells transformed with various plasmids were carried out as follows: overnight cultures of T7A49 cells (harboring two plasmids: pACYC184, and either pT7EGSCAT1, pT7EGSAMP, or pNT7APHH) in LBCarb/Cm (LB medium supplemented with 50 μg/ml carbenicillin and 5 μg/ml chloramphenicol) were diluted to $A_{600}$=0.5 in LBCarb/Cm and the cultures were incubated at 37° C. Cell growth was followed by measuring $A_{600}$. Cells were diluted and plated on LP plates, LBAmp plates and LB plates containing different concentrations of chloramphenicol.

FIG. 2 shows the growth rates in liquid culture of drug-resistant cells that harbor EGSs directed against the $Cm^R$ mRNAs and $Amp^R$ mRNAs. Plasmids employed are pACYC 184 that contains the $Cm^R$ gene (all cultures in FIG. 2) in combination with pNT7APHH that contains an EGS directed against the mRNA for alkaline phosphatase (Guerrier-Takada et al. (1995); Li and Altman, Nucleic Acids Res. 24:835–842 (1996); open circles in FIGS. 2D, 2E, and 2F)), pT7EGSCAT1 that contains an EGS directed against the mRNA for chloramphenicol transacetylase (triangles in FIGS. 2D, 2E and 2F), pKBEGSCAT1 that contains an EGS directed against mRNA for chloramphenicol transacetylase (triangles in FIGS. 2A, 2B and 2C) and pKBEGSAMP that contains an EGS directed against mRNA for β-lactamase (open squares in FIGS. 2A, 2B and 2C). Numbers in parentheses indicate the concentrations of drugs used. The pKB plasmids have the EGS genes cloned downstream from the E. coli promoter for M1 RNA rather than downstream from the T7 promoter.

As demonstrated by the results, the cells that contained plasmid pACYC184 and pUC19 with no or a non-specific EGS grew well in concentrations of Cm up to 70 μg/ml and carbenicillin (Carb) up to 500 μg/ml, whereas cells with the appropriate, specific EGS failed to grow in much lower concentrations of drug (see FIG. 2) as assayed in liquid culture. Similar results were obtained when the cells were plated onto agar.

If the liquid cultures or the plate cultures were incubated sufficiently long (for example, greater than five hours for liquid cultures; greater than two days for plates), some resistant bacteria reappeared. In fact, these viable cells had lost the plasmid harboring the EGS genes. Loss of plasmid from a single cell during the first overnight incubation can account for the appearance of viable cells.

In those cells that contained inducible T7 RNA polymerase and EGS genes under control of a T7 promoter, efficient phenotypic conversion was observed in the absence or presence of the inducer isopropyl β-d-thiogalactoside (IPTG) because of leaky transcription of the T7 polymerase gene. In these cells, in the presence of IPTG (FIGS. 2C and 2F), phenotypic conversion is more efficient than in cells that harbor EGS genes under the control of the *E. coli* promoter, presumably because the steady-state copy number of EGS RNA is higher in the former cells and the hairpin structure of the T7 transcription terminator sequence protects the EGS RNA from 3' to 5' exonuclease degradation.

Figure 2B:
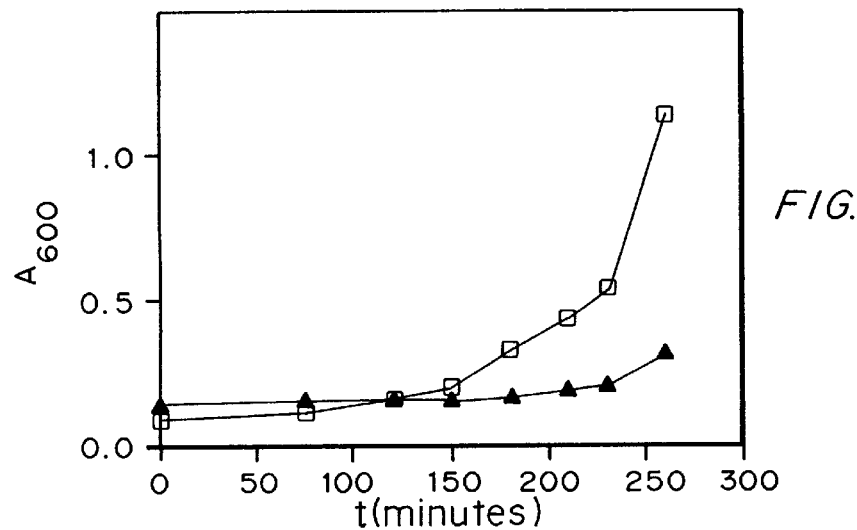
Figure 2C:
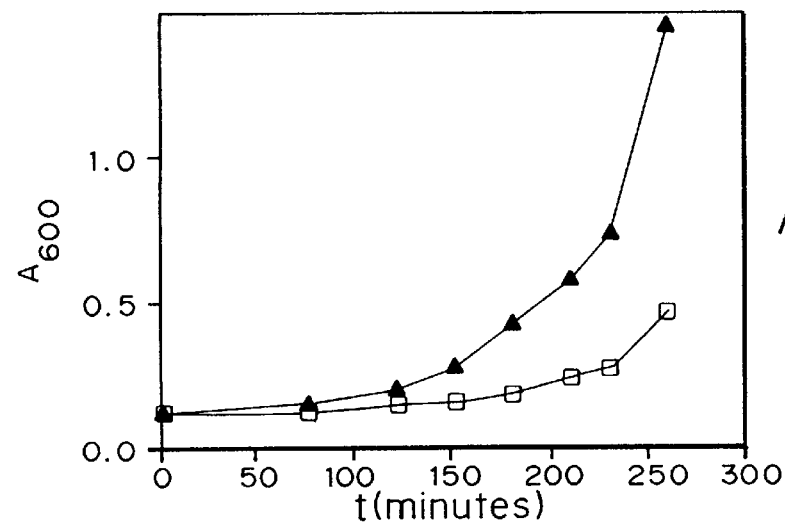
Figure 2D:
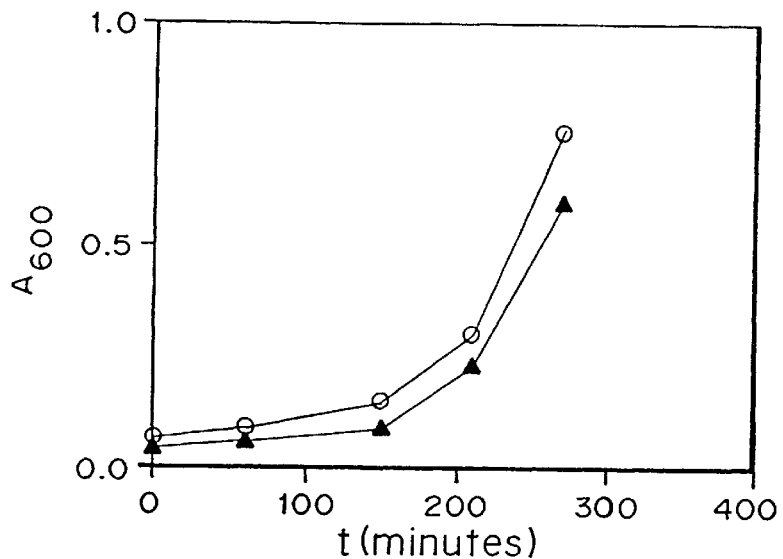
FIGS. 2D, 2E and 2F are is growth curves of BL21(DE3) cells carrying two plasmids: pACYC184+pNT7APHH (open circles) and pACYC184+pT7EGSCAT1 (triangles), graphing growth over time (min) at 50 Carb/5 Cm (FIG. 2D), 50 Carb/70 Cm (FIG. 2E), and 50 Carb/70 Cm plus IPTG (FIG. 2F).
Figure 2E:
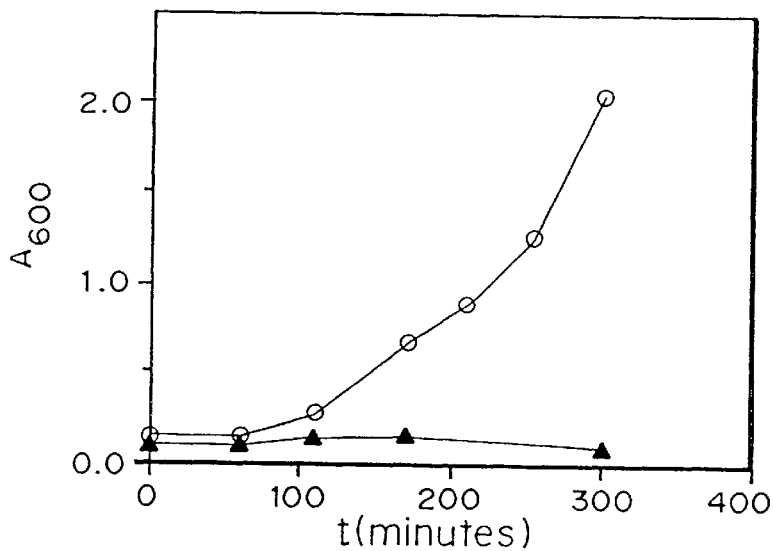
Figure 2F:
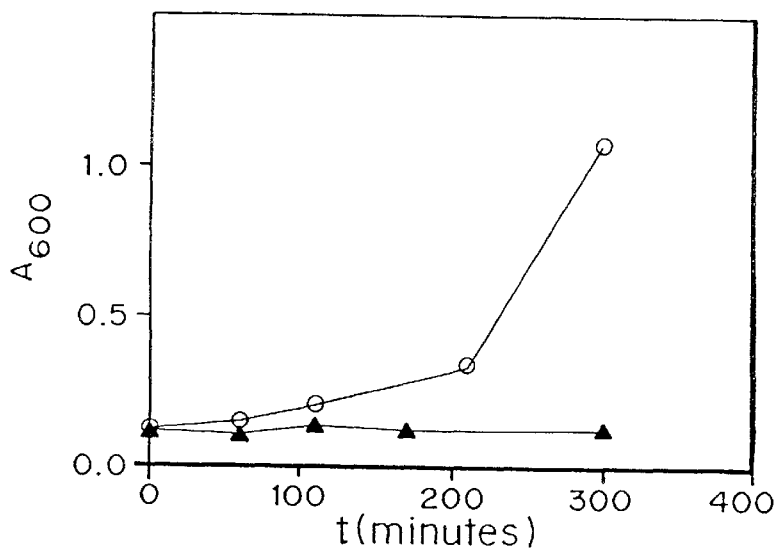

Cells harboring synthetic genes coding for EGSAMP grow well in Carb (an analog of ampicillin that is a superior selective agent) at concentrations up to 50 μg/ml (FIG. 2B, middle). However, the EGS gene in these cells is on the same derivative of the high copy number plasmid pUC19 as the $Amp^R$ marker (and is under control of an *E. coli* promoter). Therefore, the ratio of Amp mRNA to EGSAMP in these cells is expected to be more nearly equal than that of CAT mRNA to EGSCAT1 in the strains described above. Consequently, phenotypic conversion is virtually complete at 500 μg/ml Carb (FIG. 2C, bottom).

This method of phenotypic conversion can be further enhanced by, for example, determining additional sites in the target mRNA that will hybridize efficiently with an EGS to form very susceptible substrates for RNAase P, by cloning multiple EGS genes (that will hybridize with the same and/or different sites in the target mRNA) into the carrier plasmid, by increasing the copy number of the plasmid and by increasing promoter strength upstream from the EGS genes, thereby elevating the EGS-to-target mRNA ratio.

Example 2

Effect of Multiple EGSs and Ratio of EGS to Target RNA

This example describes tests of the effect of multiple EGSs targeted to the same mRNA, increasing the copy number of the EGS-encoding plasmid, and increasing the ratio of EGS to target RNA using CAT mRNA as the target.

EGSs were designed to hybridize to sites in CAT mRNA in addition to the one targeted by the EGSCAT1 described in Example 1. First, the secondary structure of the entire CAT mRNA sequence was modeled with an energy minimization program (Zucker and Stiegler, *Nucl. Acids Res.* 9:133–148 (1981)) and a target site was chosen (nucleotides 156–171 in the coding region of the CAT mRNA) on the basis of the prediction that it would be single-stranded and that the first nucleotide downstream of the intended site of cleavage by RNase P would be G. Prior to the synthesis and testing of the new EGS (EGSCAT2; SEQ ID NO:5), a fragment of CAT mRNA transcribed in vitro that contained 225 nucleotides proximal to the initiator AUG was probed with nucleases S1 (specific for single-stranded regions) and V1 (specific for hydrogen-bonded regions) and dimethyl sulfate to ascertain that the new target site was indeed in a single-stranded region. The fragment of CAT RNA was then tested as a target substrate in the presence of EGSCAT2 in vitro. The efficiency of cleavage with EGSCAT2 was much less than with EGSCAT1 and this difference was also reflected in assays of EGSCAT2 function in vivo described below.

A synthetic gene coding for EGSCAT2 under control of the promoter for M1 RNA was constructed as described for the case of EGSCAT1. Furthermore, a new construct was made (FIG. 1B, bottom) in which the two EGSs were placed in tandem with hammerhead ribozymes of the appropriate sequences that were inserted at intervals to guarantee the release of the individual EGSs from the gene transcript by appropriate processing after transcription. The new constructs were inserted into pUC19 as described in Example 1 to create the pKB series of plasmids and these plasmids were then transformed into *E. coli* BL21(DE3) that harbors pACYC184.

Figure 3A:
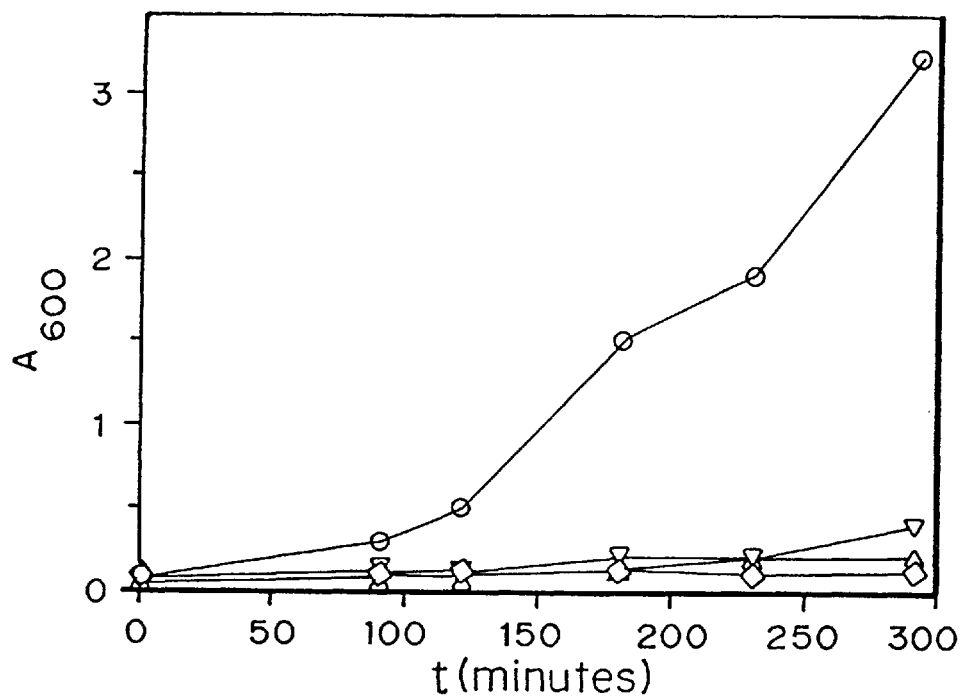
FIGS. 3A, 3B, 3C, and 3D are growth curves of RS7027 (FIGS. 3A and 3C) or BL21(DE3) (FIGS. 3B and 3D) cells carrying pKB283 (circles), pKBEGSCAT1 (triangles), pKBEGSCAT2 (inverted triangles), and pKBEGSCAT1+2 (diamonds), graphing growth over time (min) in the presence of 5 $\mu$g/ml Cm (FIG. 3A), 5 $\mu$g/ml Cm (FIG. 3B), 25 $\mu$g/ml Cm (FIG. 3C), 70 $\mu$g/ml Cm (FIG. 3D). BL21(DE3) cells also carried pACYC184. All cultures were grown in the presence of 50 $\mu$g/ml Carb.
Figure 3B:
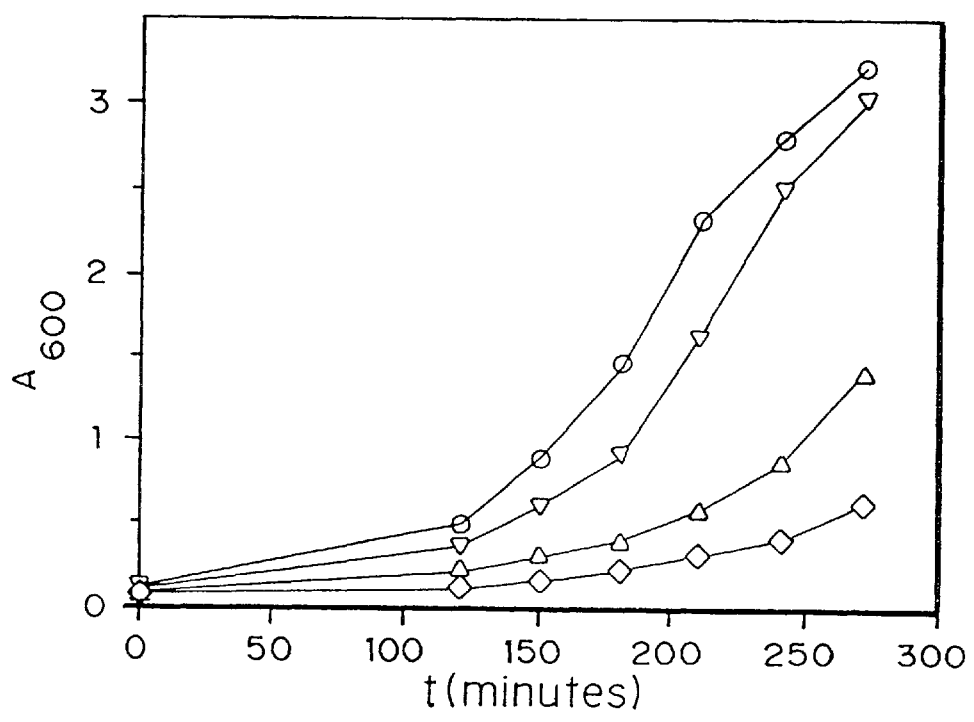
Figure 3C:
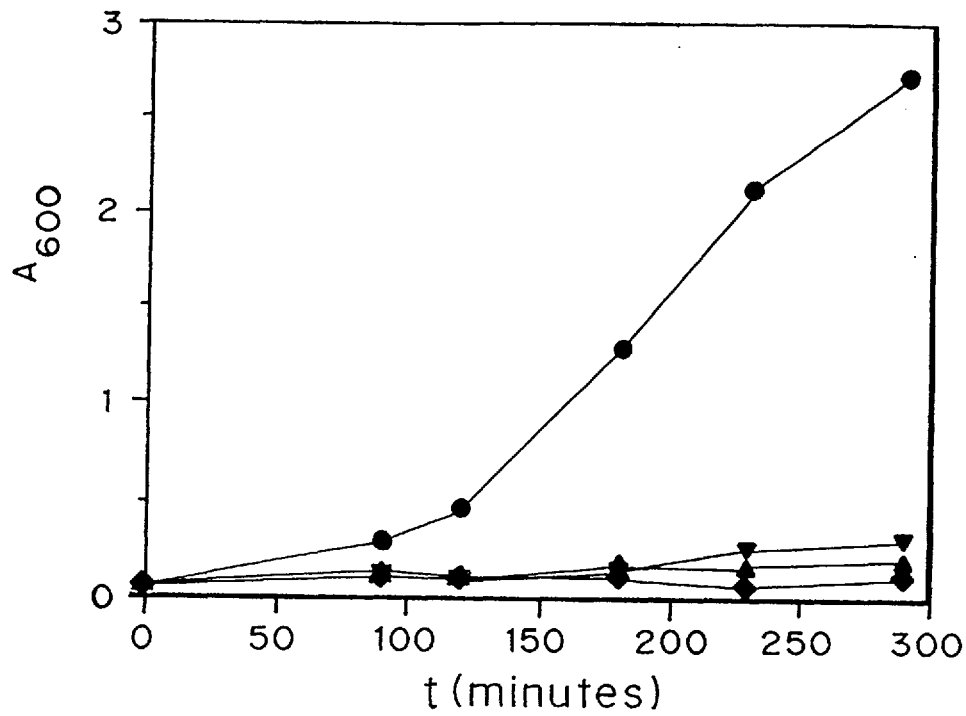
Figure 3D:
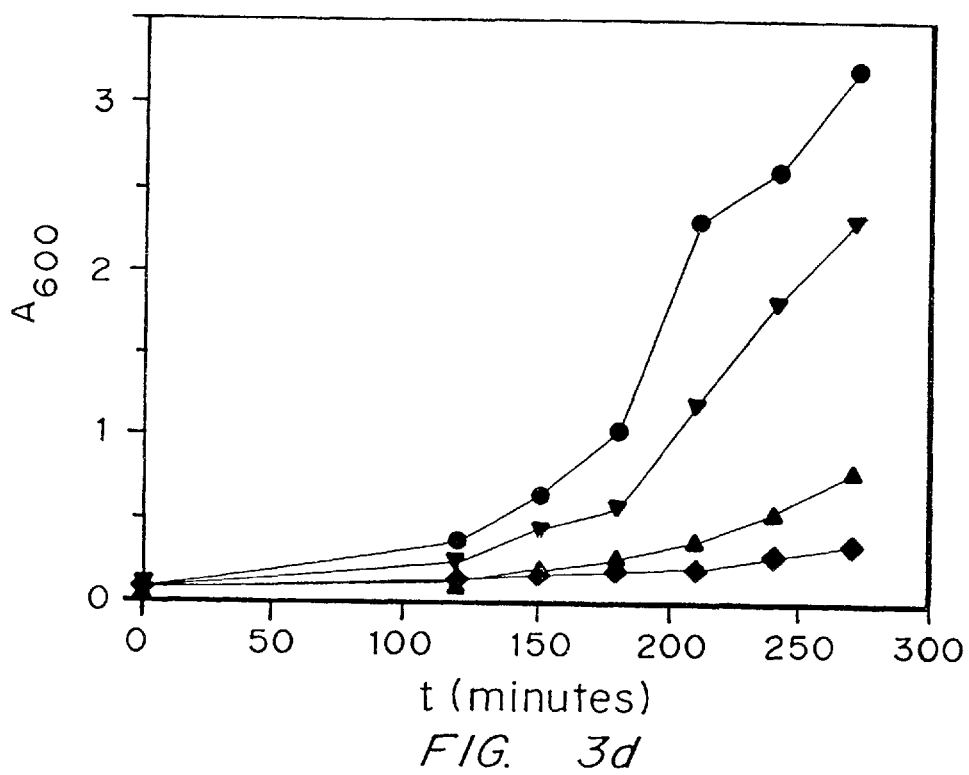

The growth properties of the strains that contain genes coding for one of the two EGSs, or both EGSs, are shown in FIGS. 3B and 3D. It is apparent both that EGSCAT2 is less effective than EGSCAT1 in converting the phenotype of the $Cm^R$ cells and also that having both EGSs in the same cell is more effective than EGSCAT1 alone. If fact, the result with both EGSs under the control of an *E. coli* promoter is as good if not better than with EGSCAT1 under the control of the T7 promoter at high levels of induction of T7 RNA polymerase. The inhibitory effect is the sum of the inhibition by the two EGSs separately. These results verify the simple hypothesis that, given the same level of EGS RNA synthesis, EGSs attacking multiple sites should be more efficient than EGSs targeted to one site only.

To increase the EGS-to-target mRNA ratio in a way different from that described above, the pKB plasmids described above were transformed into a strain, RS7027(Tn 9), in which the $Cm^R$ gene exists in single copy only on the host chromosome (Wertman et al., *Gene* 49:253–262 (1986)). The ratio of EGS to target mRNA is manipulated in this case by decreasing the copy number of the cat gene rather than increasing the level of EGS RNA. A comparison of the growth rates in FIGS. 3A and 3C with those in FIGS. 3B and 3D validates further the statement that an increase, by whatever means, of the EGS-to-target MnRNA ratio, results in increased efficiency of phenotypic conversion. In these experiments, a cytocidal effect is seen at 5 μg/ml of Cm. Additionally, cells that harbored CATEGSs that were diluted from overnight cultures (70 μg/ml Cm) into fresh medium that contained no Cm had very low viability. The low viability after dilution was not due to a nonspecific effect of EGS expression because cells that expressed the EGSs but had no cat genes were perfectly viable in the absence of Cm. furthermore, the amount of CAT enzyme in cells harboring both EGS genes, at 3 hours after dilution from overnight cultures, was less than 25% of that found in cells with no EGS genes. Not more than 10% of the cells that contained EGSs CAT1 and CAT2 were viable at 3 hours after dilution; these particular cells, which have lost the plasmid bearing the EGS genes, may account for the residual CAT activity.

Similar experiments, with similar results, both in vitro and in vivo, were carried out with three additional EGSs selected to target other, phylogenetically conserved sites in the CAT mRNA. In all cases reported here, cells that harbor EGSs are still in exponential phase while the control cells are in stationary phase after six hours of growth in liquid culture.

To ascertain that phenotypic conversion was accompanied by the expected changes in the accumulation of CAT mRNA and complementary EGS RNAs, the intracellular RNA of relevant bacterial strains was examined by Northern blot analysis. This analysis was performed by extracting total RNA from cells in the exponential phase of growth, resuspending the RNA (4 μg) in 6 M urea, and subjecting it to electrophoresis in a 2.5%, nondenaturing agarose gel in 1×TEB (89 mM Tris-borate/2.5 mM EDTA-$Na_2$, pH 8.3). The gel contained 0.5 μg/ml ethidium bromide, and electrophoresis lasted approximately 2 hours at 5 to 10 V/cm or until the bromphenol blue dye had migrated 8 cm. Resolution of the major RNA species was checked on a UV trans-illuminator. The RNAs (including 23S RNA) were electrotransferred to a nylon membrane for 12 to 15 hours at 250 mA as described by Guerrier-Takada et al., *Proc. Natl. Acad. Sci. USA* 92:11115–11119 (1995). M1 RNA (estimated at 400 copies/cell) was used as an internal standard to normalize amounts of RNA in each lane. Hybridization was performed in rapid hybridization buffer according to directions of the manufacturer (Amersham).

One complication in the interpretation of these experiments arises from the fact that the transcription, but not the translation, of CAT mRNA is enhanced under conditions of slow growth (Meyer and Schottel, *Mol. Microbiol.* 6:1095–1104 (1992)). An increase in the total amount of CAT mRNA (total of both intact mRNA and degradation products) in the strains that harbor genes that code for the EGSs was observed compared with the strains with no EGS or EGSCAT2, and that increase is correlated with the decrease in growth rate. The presence of degradation products that had the expected size (less than 732 nucleotides) as a result of cleavage of the mRNA by RNAase P were prominent on the gels. The amount of EGS RNA was quantitated in separate Northern blots and all estimates of RNA copy number (Table 1) were normalized to the amount of M1 RNA in the cells.

TABLE 1

Copy Number of CAT mRNA, its degradation products, and CATEGS in vivo

| Plasmid | EGS | Intact mRNA | Total mRNA | Intact mRNA/ Total mRNA |
|---|---|---|---|---|
| pKB283 |  | 8 | 56 | 0.14 |
| pKBEGSCAT1 | 163 | 9 | 230 | 0.04 |

TABLE 1-continued

Copy Number of CAT mRNA, its degradation products, and CATEGS in vivo

| Plasmid | EGS | Intact mRNA | Total mRNA | Intact mRNA/ Total mRNA |
|---|---|---|---|---|
| pKBEGSCAT2 | 80 | 7 | 72 | 0.10 |
| pKBEGSCAT1 + 2 | 77 | 29 | 841 | 0.03 |
| pKB283 |  | 6 | 52 | 0.12 |
| pKBEGSCAT1 | 208 | 9 | 357 | 0.03 |
| pKBEGSCAT2 | 74 | 10 | 90 | 0.11 |
| pKBEGSCAT1 + 2 | 70 | 24 | 792 | 0.03 |

A rough quantitation of the amounts of EGS and CAT mRNA indicate that in the cells harboring EGSCAT1 and EGSCAT2, in which the growth rate is slowest, the total amount of CAT mRNA and its degradation products is highest and also that the combination of EGSCAT1 and EGSCAT2 is most efficient in degrading CAT mRNA as judged by the ratio of EGS RNA to CAT mRNA and its degradation products. Additionally, the ratio of "intact" CAT mRNA (732 nucleotides or greater) to total CAT mRNA (intact plus degradation products) was lowest in cells that contained both EGSs (Table 1). This ratio was almost the same for EGSCAT1 alone.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A vector encoding an external guide sequence comprising
    an oligonucleotide having at its 5' terminus nucleotides complementary to the nucleotides 3' to a specific cleavage site in an RNA molecule to be cleaved, and at its 3' terminus the nucleotides N C C A joined to the complementary nucleotides, wherein N is any nucleotide and the complementary nucleotides in the oligonucleotide hybridize to the complementary nucleotides in the RNA molecule to be cleaved,
wherein the RNA molecule is in a bacterial cell and is involved in conferring antibiotic resistance to the cell,
wherein the external guide sequence promotes cleavage by RNAase P of the RNA molecule at the cleavage site,
wherein the vector is harbored by a second bacterial cell.

2. The vector of claim 1 wherein the complementary nucleotides include at least fifteen nucleotides.

3. The vector of claim 1 wherein the complementary nucleotides include at least seven nucleotides.

4. The vector of claim 1 wherein the vector is a phage or viral vector or a promiscuous plasmid vector.

5. The vector of claim 4 wherein the vector is plasmid R1-drd-19 or R388.

6. A vector encoding an external guide sequence comprising
    an oligonucleotide having at its 5' terminus nucleotides complementary to the nucleotides 3 ' to a specific cleavage site in an RNA molecule to be cleaved, and at its 3' terminus the nucleotides N C C A joined to the complementary nucleotides, wherein N is any nucleotide and the complementary nucleotides in the oligonucleotide hybridize to the complementary nucleotides in the RNA molecule to be cleaved,
wherein the RNA molecule is in a bacterial cell and is involved in conferring antibiotic resistance to the cell,
wherein the external guide sequence promotes cleavage by RNAase P of the RNA molecule at the cleavage site,
wherein the vector is a phage or viral vector or a promiscuous plasmid vector.

7. The vector of claim 6 wherein the vector is harbored by a second bacterial cell.

8. A method for converting the phenotype of an antibiotic-resistant bacterial cell to an antibiotic-sensitive phenotype comprising
    bringing into contact a vector encoding an external guide sequence and an antibiotic-resistant bacterial cell, wherein the vector is harbored by a second bacterial cell, wherein the cell contains an RNA molecule involved in conferring antibiotic resistance to the cell,
    wherein the external guide sequence comprises
        an oligonucleotide having at its 5' terminus nucleotides complementary to the nucleotides 3' to a specific cleavage site in the RNA molecule, and at its 3' terminus the nucleotides N C C A joined to the complementary nucleotides, wherein N is any nucleotide and the complementary nucleotides in the oligonucleotide hybridize to the complementary nucleotides in the RNA molecule,
wherein the external guide sequence promotes cleavage of the RNA molecule by RNAase P thereby converting the phenotype of the antibiotic-resistant bacterial cell to an antibiotic-sensitive phenotype.

9. The method of claim 8 wherein the complementary nucleotides include at least fifteen nucleotides.

10. The method of claim 8 wherein the complementary nucleotides include at least seven nucleotides.

11. The method of claim 8 wherein the step of bringing into contact is accomplished by administering the second bacterial cell to an animal or plant infected by the antibiotic resistant bacterial cell.

12. The method of claim 8 further comprising bringing into contact the antibiotic sensitive bacterial cell and the antibiotic to which the antibiotic resistant bacterial cell is resistant.

13. The method of claim 8 wherein the vector is a phage or viral vector or a promiscuous plasmid vector.

14. The method of claim 13 wherein the vector is plasmid R1-drd-19 or R388.

\* \* \* \* \*

UNITED STATES PATENT AND TRADEMARK OFFICE
CERTIFICATE OF CORRECTION

PATENT NO. : 5,976,874
DATED : November 2, 1999
INVENTOR(S) : Sidney Altman and Cecilia Guerrier-Takada It is certified that error appears in the above-identified patent and that said Letters Patent is hereby corrected as shown below:

Column 1,
Line 14, above the heading "BACKGROUND OF THE INVENTION", please insert the following:

-- STATEMENT REGARDING FEDERALLY SPONSORED RESEARCH OR DEVELOPMENT
  This invention was made with government support under Grant No. GM14922 awarded by the National Institutes of Health. The government has certain rights in the invention. --

Signed and Sealed this

Second Day of March, 2004

JON W. DUDAS
*Acting Director of the United States Patent and Trademark Office*